United States Patent [19]
Groffen et al.

[11] Patent Number: 5,491,283
[45] Date of Patent: Feb. 13, 1996

[54] BRC/ABL TRANSGENIC ANIMALS AS MODELS FOR PHILADELPHIA CHROMOSOME POSITIVE CHRONIC MYELOGENOUS AND ACUTE LYMPHOBLASTIC LEUKEMIA

[75] Inventors: John Groffen; Nora Heisterkamp; Paul K. Pattengale, all of Los Angeles, Calif.

[73] Assignee: Childrens Hospital of Los Angeles, Los Angeles, Calif.

[21] Appl. No.: 3,951

[22] Filed: Jan. 14, 1993

Related U.S. Application Data

[63] Continuation of Ser. No. 440,062, Nov. 22, 1989, abandoned.

[51] Int. Cl.$^6$ ................................................. C12N 15/00
[52] U.S. Cl. ................ 800/2; 800/DIG. 1; 435/172.3; 435/240.2; 435/320.1; 435/317.1; 935/70; 935/111
[58] Field of Search ................................ 800/2, DIG. 1; 435/172.3, 240.2, 320.1, 317.1; 935/70, 111

[56] References Cited

U.S. PATENT DOCUMENTS 4,736,866  4/1988  Leder et al. ................................. 800/2

OTHER PUBLICATIONS

Knight et al., Proc. Natl. Acad. Sci. 85: 3130–3134 (1988).
Wilmut et al., New Scientist, 7 Jul. 1988, pp. 56–59.
Kurzrock et al., New England J. Medicine 319(15): 990–998 (1988).
Van Brunt, Biotechnology 6(10): 1149, 1151, 1152, 1154 (1988).
McLaughlin et al., Mol. Cell. Biol. 9(5): 1866–1874 (1989).
Haricharan et al., Mol. Cell. Biol. 9(7): 2798–2805 (1989).
Gossler et al., Proc. Natl. Acad. Sci. 83: 9065–9069 (1986).
Palmiter et al., Science 222: 809–814 (1983).
Konopka et al., Biochim. Biophys. Acta 823: 1–17 (1985).

*Primary Examiner*—Jasemine C. Chambers
*Attorney, Agent, or Firm*—Pennie & Edmonds

[57] ABSTRACT

The present invention relates to non-human transgenic animals which contain a transgene comprising a BCR/ABL gene fusion and which develop leukemia. In a preferred embodiment of the present invention, the transgenic animals exhibit a rapid induction of acute leukemia.

The present invention offers the advantage of providing, for the first time, a non-human transgenic animal model system which carries the BCR/ABL gene fusion characteristic of the Philadelphia chromosome and which develops leukemia in a manner directly analogous to the clinical progression of chronic myelogenous leukemia (CML) and/or acute lymphoblastic leukemia (ALL) in humans. This model system for human leukemia may be valuable in obtaining a better understanding of CML and ALL and in developing effective therapeutic regimens.

15 Claims, 11 Drawing Sheets

BRC/ABL TRANSGENIC ANIMALS AS MODELS FOR PHILADELPHIA CHROMOSOME POSITIVE CHRONIC MYELOGENOUS AND ACUTE LYMPHOBLASTIC LEUKEMIA

This is a continuation, of application Ser. No. 07/440,062, filed Nov. 22, 1989 now abandoned.

INTRODUCTION

The present invention relates to transgenic non-human animals which contain a transgene comprising a BCR/ABL gene fusion and which develop leukemia. The nonhuman transgenic animals of the invention may serve as valuable models for chronic myelogenous and acute lymphoblastic leukemia in humans.

BACKGROUND OF THE INVENTION

CHRONIC MYELOGENOUS AND ADULT LYMPHOBLASTIC LEUKEMIA

Leukemia is a malignant condition of white blood cells in which bone marrow is diffusely replaced by relatively immature white blood cells which generally also appear, in large numbers, in the circulating blood (Robbins and Angell, 1976, in "Basic Pathology", Second Edition, W. B. Saunders Co., Philadelphia, pp. 349–354). Leukemias may be classified as acute lymphocytic (or lymphoblastic), chronic lymphocytic, acute myelogenous, or chronic myelogenous.

Chronic myelogenous leukemia (CML) accounts for approximately 25 percent of all leukemias. Onset of the disease occurs most frequently in middle age, with males and females affected approximately equally. CML is generally associated with prominent enlargement of the spleen. Prognosis for survival is approximately three to four years.

The clinical progression of CML may be divided into two phases, a chronic phase and a blastic phase (Canellos (1983) in "Harrison's Principles of Internal Medicine", Petersdorf et al., eds., Tenth Edition, McGraw Hill Book Company, N.Y., pp. 808–810). During the chronic phase, there is a proliferation and accumulation of polymorphonuclear leukocytes and granulocytic (myeloid) cells of intermediate maturity; myeloblasts usually account for less than ten percent of cells in the bone marrow and peripheral blood. The chronic phase typically persists for a median of 36 to 40 months before the onset of the blastic phase. During the blastic phase, there is a dramatic increase in the number of undifferentiated cells. In about one third of CML blastic phase cases, the blast cell morphology has some of the characteristics of lymphoblasts, including expression of the enzyme terminal deoxynucleotidyl transferase and reactivity with a non-B, non-T anti-acute lymphoblastic leukemia antiserum.

Acute lymphocytic (or lymphoblastic) leukemia accounts for about 20 percent of all leukemias, occurs predominantly in children, and develops more frequently in males than in females. Untreated, the prognosis for survival is approximately four months; with treatment, survival may be for several years and some cures have been reported (Robbins and Angell, supra). The leukemic cells of about 75 percent of patients with ALL are often termed "null" cells because they lack B and T cell markers.

THE PHILADELPHIA CHROMOSOME

The Philadelphia (Ph) chromosome is a cytogenetic hallmark of CML. It is the result of a reciprocal translocation t(9;22)(q34;q21) which is found specifically in the leukemic cells of over 95% of chronic myelogenous leukemia (CML) patients (Rowley, 1973, Nature 243:290–293; de Klein et al., 1982, Nature 300:765–767). In addition, it occurs in 25–30% of adult and 2–10% of pediatric patients with acute lymphocytic leukemia (ALL) (Sandberg et al., 1980, Cancer Genet. Cytogenet. 2:145–174; Priest et al., 1980). The presence of the Philadelphia chromosome in ALL has been associated with a worse prognosis, particularly in children (Robeiro et al., 1987, Blood 70: 948). The genes located at the breakpoints on both chromosomes have been identified; the ABL oncogene located at 9q34 is translocated to chromosome 22q11, where it is fused in a head-to-tail fashion to 5' exons of the BCR gene (de Klein et al., 1982, Nature 300:765–767; Heisterkamp et al., 1985, Nature 315:758–761; Shtivelman et al., 1985, Nature 315:550–554). In CML, the breakpoints on chromosome 22 are clustered within a small (5.8 kb) region (the major breakpoint cluster region, Mbcr) located in the middle of the BCR gene (Groffen et al., 1984, Cell 36:93–99). In ALL, a heterogeneity with respect to the breakpoints in the BCR gene exists (Rodenhuis et al., 1985, N. Engl. J. Med. 313:51–52; Erikson et al., 1986, Proc. Natl. Acad. Sci. U.S.A. 83:1807–1811; de Klein et al., 1986, Blood 68:1369–1375); some patients have a breakpoint within Mbcr, whereas in others, the break occurs within the first intron of the BCR gene (Heisterkamp et al., 1988, Nucl. Acids Res. 16:10069–10081; Hermans et al., 1987, Cell 51:33–40). The majority of pediatric Ph-positive ALL patients have a breakpoint of the latter type (Heisterkamp et al., 1989, Blood 73:1307–1311). In all cases, the translocation results in the transcription of a chimeric BCR/ABL mRNA which is translated into a BCR/ABL fusion protein (for an overview, see: Kurzrock et al., 1988, N. Engl. J. Med. 319:990–998).

Two distinct BCR/ABL fusion proteins have been identified; in CML and in adult Ph-positive ALL, a phosphoprotein of 210,000 MW (P210) is found, which contains a substantial amino-terminal BCR component (Shtivelman et al., 1985, Nature 315:550–554; Mes-Masson et al., 1986, Proc. Natl. Acad. Sci. U.S.A. 83:9768–9772); the chimeric P190 protein found in juvenile and adult Ph-positive ALL in which the break point occurs within the BCR gene contains only those BCR amino acid residues encoded by its first exon (Hermans et al., 1987, Cell 51:33–40; Fainstein et al., 1987, Nature 330:386–388). Both P210 and P190 contain all the amino acids of the ABL oncogene except those encoded by its first exon; they exhibit an abnormal tyrosine kinase activity and are strongly autophosphorylated in vitro (Konopka et al., 1984, Cell 37:1035–1042; Kloetzer et al., 1985, Virology 140:230–238; Chan et al., 1987, Nature 325:635–637; Clark et al., 1987; Kurzrock et al., 1987, Nature 325:631–635). Although the presence of the Ph chromosome is used as a diagnostic marker and the BCR/ABL fusion protein is invariably found in Ph-positive patients, very little is known about the direct role of BCR/ABL in the pathogenesis of leukemia.

TRANSGENIC ANIMALS

The term "transgenic animals" refers to non-human animals which have incorporated a foreign gene into their genome; because this gene is present in germline tissues, it is passed from parent to offspring. Exogenous genes are introduced into single-celled embryos (Brinster et al., 1985, Proc. Natl. Acad. Sci. U.S.A. 82:4438–4442). Transgenic mice have been shown to express globin (Wagner et al., 1981, Proc. Natl. Acad. Sci. U.S.A. 78:6376–6380), transferrin (McKnight et al., 1983, Cell 34:335–341), immunoglobulin (Brinster et al., 1983, Nature 306:332–336; Ritchie et al., 1984, Nature 312:517–520; Goodhardt et al., 1987, Proc. Natl. Acad. Sci. U.S.A. 84:4229–4233; Stall et al., 1988, Proc. Natl. Acad. Sci. U.S.A. 85:3546–3550), human major histocompatibility complex class I heavy and light chain (Chamberlain et al., 1988, Proc. Natl. Acad. Sci. U.S.A. 85:7690–7694), functional human interleukin-2 receptors (Nishi et al., 1988, Nature 331:267–269), rat myosin light-chain 2 (Shani, 1985, Nature 314:283–286), viral oncogenes (Small et al., 1985, Mol. Cell. Biol. 5:642–648), and hepatitis B virus (Chisari et al., 1985, Science 230:1157–1163) genes, to name but a few. Rearrangement of immunoglobulin genes has been observed in transgenic mice (Goodhardt et al., 1987, Proc. Natl. Acad. Sci. U.S.A. 84:4229–4233; Bucchini et al., 1987, Nature 326:409–411). Krimpenfort et al. (1987, EMBO J. 6:1673–1676) generated transgenic mice that showed cell surface expression of HLA-B27 antigen biochemically indistinguishable from HLA-B27 in human cells by crossing one strain of transgenic mice carrying the HLA-B27 heavy chain gene with mice carrying the transgenic $\beta_2$ microglobulin gene.

TRANSGENIC ANIMAL MODELS FOR HUMAN CANCERS

Transgenic animals have been observed to express deregulated oncogenes and develop tumors (Stewart et al., 1984, Cell 38: 627–637; Adams et al., 1985, Nature 318: 533–538; Hanahan, 1985, Nature 315: 115–122; Lacey et al., 1986, Nature 322: 609–612; Palmiter and Brinster, 1986, Annu. Rev. Genet. 20: 465–499; Cory and Adams, 1988, Annu. Rev. Immunol. 6:25–48). In particular, a number of transgenic animals have been developed as model systems for the study of white blood cell disorders.

Lohuizen et al. (1989, Cell 56: 673–682) developed transgenic mice bearing the pim-1 gene supplemented with an upstream immunoglobulin murine leukemia virus long terminal repeat. The pim-1 gene has been found to be activated by proviral insertion in murine leukemia virus-induced T cell lymphomas (Cuypress et al., 1984, Cell 37: 141–150; Mucenski et al., 1987, Oncogene Res. 2: 33–48). Between five and ten percent of the transgenic mice developed by Lohuizen et al. were observed to develop T cell lymphomas before 7 months of age, and more frequently when newborn mice were infected with murine leukemia virus.

Knight et al. (1988, Proc. Natl. Acad. Sci. U.S.A. 85.: 3130–3134) developed transgenic rabbits bearing the rabbit C-MYC oncogene fused with the rabbit immunoglobulin heavy chain gene enhancer. The transgenic rabbits were observed to develop what appeared to be an oligoclonal lymphocytic leukemia by the age of 17 to 21 days. Interestingly, mice bearing a similar transgene were observed to develop B cell lymphomas at a later stage of development (Adams et al., 1985, Nature 318: 533–538).

With regard to the BCR/ABL gene fusion associated with the Philadelphia chromosome, a BCR/ABL bearing retrovirus has been observed to transform immature B cells only after prolonged periods of cell culture (McLaughlin et al., 1987, Proc. Natl. Acad. Sci. U.S.A. 84: 6558–6562; Young and Witte, 1988, Mol. Cell. Biol. 8: 4079–4087); however, BCR/ABL was found not to transform NIH 3T3 fibroblasts (Daley et al., 1987, Science 237: 532–535). Hariharan et al. (1989, Mol. Cell. Biol. 9:2798–2805) developed transgenic mice bearing a synthetic BCR/abl gene comprising BCR and a viral abl gene (v-abl) fragment which lacks the second and a portion of the third exon, of the murine cellular abl (c-abl) gene and which also carries a substantial internal deletion. (Hariharan et al., 1988, Oncogene Res. 3: 387–399). The synthetic fused gene was combined with either the immunoglobulin heavy chain gene enhancer or a portion of the long terminal repeat from myeloproliferative sarcoma virus (Franz et al., 1986, Proc. Natl. Acad. Sci. U.S.A. 83: 3292–3296); some of the mice developed lymphomas, but not leukemias, after a variable latent period.

SUMMARY OF THE INVENTION

The present invention relates to non-human transgenic animals which contain a transgene comprising a BCR/ABL gene fusion and which develop leukemia. In particular embodiments of the present invention, the transgenic animals may exhibit a rapid induction of acute leukemia or, alternatively, a chronic myelogenous-type leukemia.

The transgenic animals of the invention carry a transgene which comprises a 5' portion of BCR exons and a 3' portion of ABL exons. In a preferred embodiment of the invention, the ABL nucleotide sequences comprise human ABL nucleotide sequences. In alternate embodiments, the transgene comprises non-human abl gene sequences. In further preferred embodiments of the invention, the transgene comprises either at least a complete third exon or a portion of the second exon of the ABL gene. In a specific embodiment of the present invention, the transgenic animals carry a transgene comprising the first exon of the BCR gene as well as at least one exon from the Mbcr region and exons 2 through 11 of the ABL gene. In a preferred specific embodiment of the present invention, the transgenic animals carry a transgene comprising the first exon of the BCR gene and exons 2 through 11 of the ABL gene.

The present invention offers the advantage of providing, for the first time, a non-human transgenic animal model system which carries the BCR/ABL gene fusion characteristic of the Philadelphia chromosome; transgenic animals of the invention have been found to develop leukemia in a manner directly analogous to the clinical progression of chronic myelogenous leukemia (CML) and/or acute lymphoblastic leukemia (ALL) in humans. This model system for human leukemia may be valuable in obtaining a better understanding of CML and ALL and in developing effective therapeutic regimens.

DEFINITIONS

ABL: the human ABL oncogene using standard nomenclature. Unless specified, ABL as used herein may refer to human or non-human nucleotide sequence.

abl: non-human oncogene corresponding to ABL.

BCR: the Breakpoint Cluster Region gene.

c: cellular.

Mbcr: the major breakpoint cluster region in which are located several of the breakpoints characteristic of the Philadelphia chromosome of CML.

Transgenic animal: a nonhuman animal which has incorporated a foreign gene into its genome.

Transgene=transgenic sequence: a foreign gene or recombinant nucleic acid construct which has been incorporated into a transgenic animal.

v: viral.

DETAILED DESCRIPTION OF THE INVENTION

Figure 1:
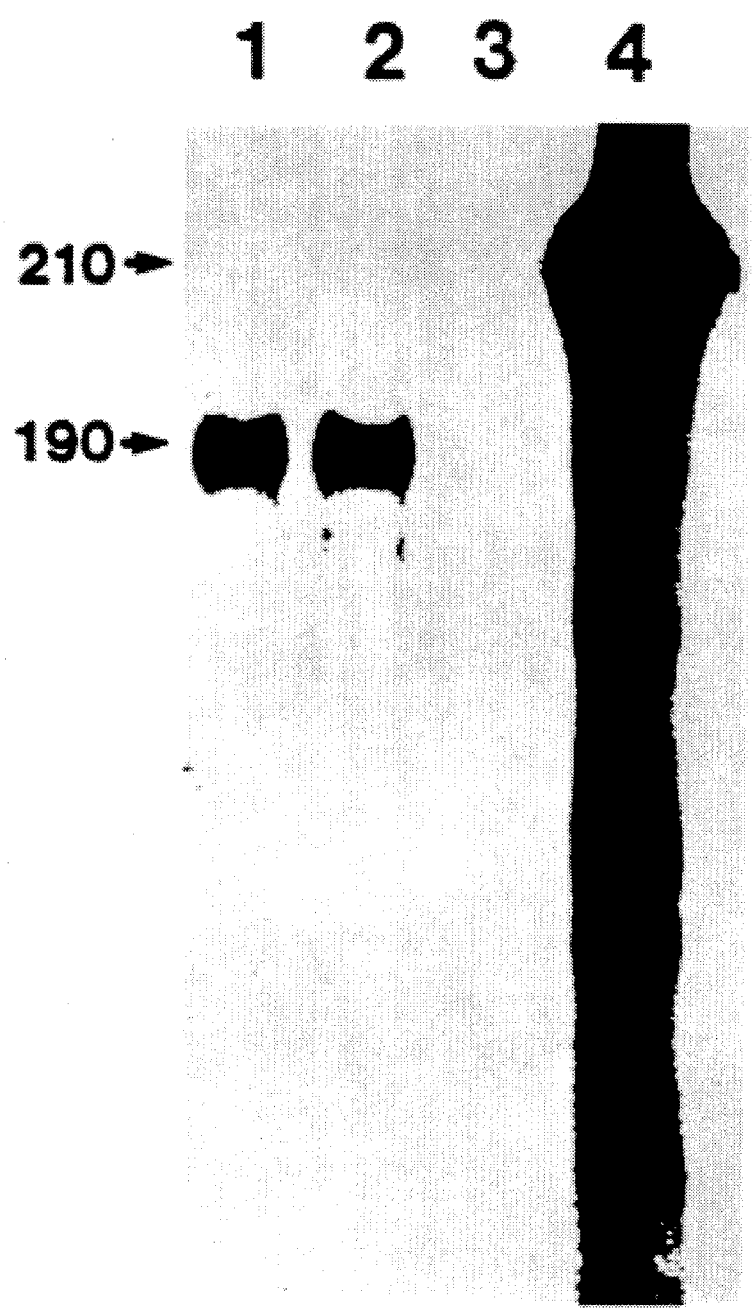
FIG. 1. Expression of P190 BCR/ABL. Two clones (lanes 1 and 2) transfected with P190/BCR produce a P190 protein, that is active in an in vitro autophosphorylation assay, whereas a third clone (lane 3) is negative. An arrow points to the P190 and to the P210 produced in K562 (lane 4).

The present invention relates to transgenic non-human animals which carry a BCR/ABL transgene and which may serve as animal models of leukemia in humans. For purposes of clarity of disclosure, and not by way of limitation, the detailed description of the invention is divided into the following subsections:

(i) BCR/ABL Recombinant Nucleic Acid Constructs (ii) Generation of Transgenic Animals (iii) Utility of the Invention.

BCR/ABL RECOMBINANT NUCLEIC ACID CONSTRUCTS

Recombinant BCR/ABL constructs may be produced using any method known in the art. BCR and ABL genes, or portions thereof, may be derived from human or non-human (abl) sources. BCR or ABL gene sequences may be obtained from the same species intended to serve as the transgenic host, although it may be preferable to use human BCR and ABL gene sequences to create a model for the gene product associated with human disease.

The ABL gene may be obtained from constructs which have been the subjects of publication and are available among those skilled in the art, such as the construct described in Heisterkamp et al. (1983, J. Mol. Appl. Gen. 2:57–68) or pALMP or pCLMP constructs of the present invention. The available ABL sequences may also be used to identify additional clones bearing ABL sequences in genomic DNA or cDNA libraries using standard hybridization techniques such as the method set forth by Benton and Davis (1977, Science 196:180) for bacteriophage libraries and Grunstein and Hogness (1975, Proc.Natl.Acad.Sci. U.S.A 72:3961–3965) for plasmid libraries, or may be used to clone ABL sequences using polymerase chain reaction (PCR) technology (Saiki et al., 1985, Science 230:1350). Similarly, BCR sequences may be obtained from publicly available constructs or using the pALMP or pCLMP constructs of the present invention in conjunction with standard colony hybridization or PCR techniques.

Alternatively, a naturally occurring BCR/ABL fused gene may be cloned from cells carrying the appropriate translocation for use according to the present invention, using standard techniques. The BCR and ABL sequences utilized may represent genomic DNA or cDNA sequences.

Portions of the BCR and ABL genes may be linked together using any technique known in the art, including the ligation of compatible restriction endonuclease fragments. According to the present invention, the fused BCR/ABL construct may comprise the first BCR exon and either the entire third exon of ABL or a portion of its second exon (see FIG. 7). If the ABL sequences are derived from human c-ABL sequences, the BCR/ABL construct may contain one or more ABL exons.

In preferred embodiments of the invention, the BCR/ABL gene fusion is engineered to resemble BCR/ABL gene fusions produced by naturally occurring translocations and found in association with Philadelphia chromosomes. For example, and not by way of limitation, the fused BCR/ABL gene may be engineered to resemble the BCR/ABL fusion found on Philadelphia chromosomes in patients with CML, and may preferably comprise the first BCR exon as well as at least one exon from the Mbcr region and the second through eleventh ABL exons of the ABL gene or a functional portion therof. A functional portion of the ABL gene is construed to refer to a portion of the ABL gene which encodes a protein which retains tyrosine kinase activity. A specific example of a construct which resembles a BCR/ABL fusion associated with CML is comprised in construct pCLMP of the prsent invention. Alternatively, and not by way of limitation, the fused BCR/ABL gene may be engineered to resemble the BCR/ABL gene frequently associated with Philadelphia chromosome positive ALL, which includes the first BCR exon and the second through eleventh ABL exon; accordingly, the constructs of the invention may comprise one BCR exon and the second through eleventh ABL exons, or a functional portion thereof. A specific example of a construct which resembles a BCR/ABL fusion associated with ALL is comprises in construct pALMP of the present invention. According to the invention, when constructs which resemble naturally occurring BCR/ABL fusions associated with CML are used to create transgenic animals, the resulting transgenic animals may develop a leukemia similar to CML, and when constructs which resemble naturally occurring BCR/ABL fusions associated with ALL are used to create transgenic animals, the resulting transgenic animals may be likely to develop a leukemia similar to ALL.

The BCR/ABL gene fusion of the invention is preferably engineered to be under the control of a suitable promoter sequence. Any promoter sequence known in the art may be used, but it is preferable that the promoter used is not particularly active during embryonic development, as such promoters, including the BCR promoter, have been associated with a high mortality rate for transgenic embryos. For this reason, strong viral promoters, such as those found in retroviral long terminal repeats, are preferably not used. Particularly useful promoters would exhibit relatively low levels of expression during embryonic development. Suitable promoters would include inducible promoters, including, but not limited to, the metallothionine promoter (Brinster et al., 1982, Nature 296: 39–42), the heat shock protein promoter, elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

The BCR/ABL gene constructs may be cloned using any method known in the art. A large number of vector-host systems known in the art may be used. Possible vectors include, but are not limited to, cosmids, plasmids or modified viruses, but the vector system must be compatible with the host cell used. Such vectors inclde, but are not limited to, bacteriophages such as lambda derivatives, or plasmids such as PBR322, pVCs or Bluescript®(Stratagene) plasmid derivatives. Recombinant molecules may be introduced into host cells via transformation, transfection, infection, electroporation, etc.

Once a BCR/ABL construct has been generated, it may preferably be tested to determine whether it results in a functional gene product. For example, the BCR/ABL construct may be co-transfected into a suitable cell line (including but not limited to the Rat-2 cell line) together with an appropriate reporter gene (such as, but not limited to, thymidine kinase activity, resistance to antibiotics, including G418 etc.). Transfected cells may then be selected and tested for expression of a BCR/ABL gene product. For example, RNA may be harvested from the cells and tested for the presence of a BCR/ABL mRNA transcript using either standard Northern blot techniques or polymerase chain reaction using appropriate oligonucleotide primers (Kowasaki et al., 1988, Proc. Natl. Acad. Sci. U.S.A. 85: 5698–5702). Preferably, the transfectants may be tested for acquisition of BCR/ABL associated tyrosine kinase activity using a standard in vitro phosphorylation assay, such as that described in Fainstein et al. (1987, Nature 330: 386–388) or tested for reactivity with anti-ABL antiserum, such as that described in Stam et al. (1987, Mol. Cell. Biol. 7: 1955–1960). In addition, protein may be harvested from the transformed cells and analyzed by SDS-polyacrylamide gel electrophoresis and/or Western blotting techniques using, for example, anti-ABL antiserum (Stam et al., supra) to determine whether a protein of appropriate molecular weight has been encode by the BCR/ABL construct. If it appears that the BCR/ABL construct is adequately expressed in the transfected cell line, the construct may then be used to produce transgenic animals.

GENERATION OF TRANSGENIC ANIMALS

The recombinant DNA molecules of the invention may be introduced into the genome of non-human animals using any method for generating transgenic animals known in the art.

In general, the scheme presently employed to produce transgenic mice involves the following: male and female mice, from a defined inbred genetic background, are mated at midnight. Twelve hours later, the female is sacrificed and the fertilized eggs are removed from the uterine tubes. At this time, the pronuclei have not yet fused and it is possible to visualize them in the light microscope. Foreign DNA is then microinjected (100–1000 molecules per egg) into a pronucleus. Shortly thereafter fusion of the pronuclei (a female pronucleus or the male pronucleus) occurs and, in some cases, foreign DNA inserts into (usually) one chromosome of the fertilized egg or zygote. The zygote is then implanted into a pseudo-pregnant female mouse (previously mated with a vasectomized male) where the embryo develops for the full gestation period of 20–21 days. The surrogate mother delivers these mice and by four weeks the pups are weaned from the mother. To test these mice for the presence of foreign DNA, a portion of the tail (a dispensable organ) is removed and the DNA extracted. DNA-DNA hybridization (in a dot blot, slot blot or Southern blot test) is employed to determine whether the mice carry the foreign DNA. Of the eggs injected, on average 10% develop properly and produce mice. Of the mice born, on average one in four (25%) are transgenic for an overall efficiency of 2.5%. Once these mice are bred they pass along the foreign gene in a normal (Mendelian) fashion linked to a mouse chromosome. Mating two homozygous mice with the transgenic DNA means 100% of the offspring carry two copies of the transgene.

When this is done it is common that the mice carry tandemly repeated copies of the foreign gene (from 1–80 copies) at one chromosomal location or site.

The present invention is not limited to any one species of animal, but provides for any non-human animal species which may be appropriate. For example, mice, guinea pigs, rabbits and pigs, sheep, cows, goats, and horses, to name but a few, may provide useful transgenic systems.

Likewise, any method known in the art may be used to produce transgenic animals, including but not limited to, microinjection, cell gun, transfection of DNA, and electroporation.

It is preferable to remove prokaryotic sequences from eukaryotic sequences prior to the introduction of eukaryotic sequences into the single-celled embryos, using techniques (e.g. gel electrophoresis) known in the art.

UTILITY OF THE INVENTION

The present invention relates to the production of non-human transgenic animals that may serve as clinically accurate models for human diseases which have been associated with BCR/ABL gene fusions resulting from chromosomal translocation, including Philadelphia chromosome positive CML and ALL. The transgenic animals of the invention provide, for the first time, an animal model system in which the BCR/ABL transgene results in the development of leukemia. As illustrated in Example Section 6, infra, in a specific embodiment of the invention, in which transgenic animals are produced which carry a BCR/ABL transgene that resembles the BCR/ABL gene fusion associated with Philadelphia chromosome positive ALL, the transgenic animals of the invention were observed to develop acute leukemia resembling ALL at an age comparable to the average age of onset of human ALL.

By serving as an accurate model for CML and ALL, the transgenic animals of the invention provide a useful system for the development of therapeutic programs for these diseases, including both chemotherapeutic and immunotherapeutic modalities. Furthermore, the transgenic animals of the invention can be used to advance basic research in these diseases.

According to an alternate embodiment of the invention, transgenic animals which carry a BCR/ABL transgene may be produced, and the bone marrow of these transgenic animals may be harvested and then used to repopulate the bone marrow of another animal, the bone marrow of which has been destroyed (e.g. by x-ray irradiation). Animals produced by this method may also be used as effective models of CML or AML, and offer the advantage of not expressing BCR/ABL in non-hematologic tissues.

Similarly, the BCR/ABL constructs may be introduced into bone marrow cells, including, but not limited to, embryonic stem cells, of a non-human animal using any method known in the art (including transfection, transformation, infection, electroporation, microinjection or cell gun) in vivo or in vitro, and the cells may then be re-introduced so that they may re-populate the bone marrow of animal. The resulting animal should contain BCR/ABL sequences in the genomic DNA of some but not all of its cells, and therefore may be considered a chimeric animal.

In addition, a useful model for the development of leukemia may be produced by generating a transgenic animal in which the BCR/ABL transgene is under the control of an inducible promoter. In a preferred embodiment of the invention, the BCR/ABL transgene may be under the control of the metallothionine promoter, such that when the transgenic animal is exposed to heavy metals, the expression of BCR/ABL may be induced and leukemia may result.

Furthermore, the transgenic animals of the invention may be used as sources of cells and tissues which may be grown in culture and which may be useful in the study of human leukemia.

EXAMPLE: GENERATION OF BCR/ABL TRANSGENIC MICE WHICH DEVELOP PHILADELPHIA CHROMOSOME POSITIVE ACUTE LEUKEMIA

MATERIALS AND METHODS

AUTOPHOSPHORYLATION ASSAY

Cellular extracts ($10^6$ cells) were prepared as described (Fainstein et al., 1987, Nature 330:386–388); in vitro phosphorylation assays were performed as described in Fainstein et al. (1987, Nature 330:386–388) using a previously described anti-ABL antiserum (Stam et al., 1987, Mol. Cell Biol. 7:1955–1960).

DNA CONSTRUCTS AND TRANSGENIC MICE

The construct was made in several steps. A 1.8 kb BglII-KpnI fragment from an ABL cosmid clone (Heisterkamp et al., 1983, J. Mol. Appl. Gen. 2:57–68) containing exon 2 was isolated; a 5 kb KpnI-EcoRI cDNA fragment containing all 3' ABL exons was ligated with the first fragment into pSK digested with BamHI and EcoRI. A genomic 7 kb EcoRI DNA fragment containing the first BCR gene exon was inserted into pSK and clones containing a 5' ClaI- 3' NotI sites were isolated. The 5' ClaI- 3' NotI BCR gene fragment was ligated with the 5' NotI - 3' ClaI ABL fragment into pSK digested with ClaI. This construct contained all coding information for P190 under control of the BCR gene promoter. To replace this promoter with that of the mouse metallothionine gene, plasmid mMT-1 was digested with SstI and BglII and the 200 bp MT promoter fragment was inserted into pSK digested with SstI and BamHI; this plasmid was opened at the 3' end of MT with a SmaI×SalI digest. A 0.7 kb fragment of the first BCR gene exon, from EagI to SalI, was blunted at the EagI site and inserted into this plasmid. The resulting promoter fragment has 13 nucleotides of the BCR gene 5' to its initiator methionine codon. A ClaI-SstI linker was inserted into the plasmid at the 5' end and the entire promoter fragment was isolated as a 5' ClaI - 3' XhoI fragment (an XhoI site is present 5' to the SalI site in the first BCR gene exon). This was ligated with a 9 kb 5' XhoI - 3' ClaI BCR/ABL fragment into pSK. Vector sequences (3 kb) were separated from the insert (14 kb) by an SstII digestion; inserts were purified by electrophoresis on low melting point agarose gels, phenol/ sodium acetate extractions (Heinsterkamp et al., 1983, J. Mol. App. Gen. 2:57–68) and passage over an elutip-D (Schleicher and Schuell) column. Microinjections into one-cell fertilized eggs were performed essentially as described (Hogan et al., 1986 in "Manipulating the Mouse Embryo", Cold Spring Harbor Press, Cold Spring Harbor, N.Y.). Southern blots were with 10 ug of DNA; blotting and hybridization were as described; a 0.6 kb XhoI-BglII fragment from the first exon of the BCR gene was used as probe.

RNA ISOLATION AND PCR ANALYSIS

RNAs were isolated using guanidine-thioisocyanate (Chomczynski and Sacci, 1987, Anal. Biochem. 162:156–159). The first strand was synthesized using MoMuLV reverse transcriptase and oligonucleotide "ALL F" as described in Kawasaki et al. (1988, Proc. Natl. Acad. Sci. U.S.A. 85:5698–5702). The polymerase chain reaction was performed as described in the accompanying manuscript using oligonucleotides "ALL E" and "ALL F" (Kawasaki et al., 1988, Proc. Natl. Acad. Sci. U.S.A. 85:5698–5702). Samples were hybridized to oligonucleotide "ALL G" (Kawasaki et al., 1988, Proc. Natl. Acad. Sci. U.S.A. 85:5698–5702).

HISTOPATHOLOGY

Complete autopsies were performed. Mice were anesthesized prior to all procedures possibly involving pain or discomfort. Mice were sacrificed using cardiac puncture; peripheral blood samples were collected from the tails of anesthesized mice. Tissue sections were fixed for hours in a mixture of 10% formalin and 90% B5 (20 g $HgCl_2$ and 4.2 g NaAc [anhydrous]in 300 ml) and stored in 70% ethanol. Peripheral blood and bone marrow smears were stained with Wright-Giemsa stain and evaluated morphologically. White blood cell (WBC) counts were performed with a hemocytometer.

RESULTS

THE P190 CONSTRUCT

In initial experiments, a DNA construct encoding P190 under control of the human BCR promoter was tested. After co-transfection of this construct with the TK (thymidine kinase) gene into Rat-2 cells in culture, colonies were picked and assayed for P190 autophosphorylation activity. Two of three lines tested (FIG. 1, lanes 1 and 2) produced substantial amounts of active P190 although the level was lower than that found in the P210-producing cell line K562 (lane 4). The two P190-producing lines both exhibited a transformed phenotype (not shown), which was evident immediately after selection on HAT medium. These experiments established that the construct encoded a functional protein.

Figure 2:
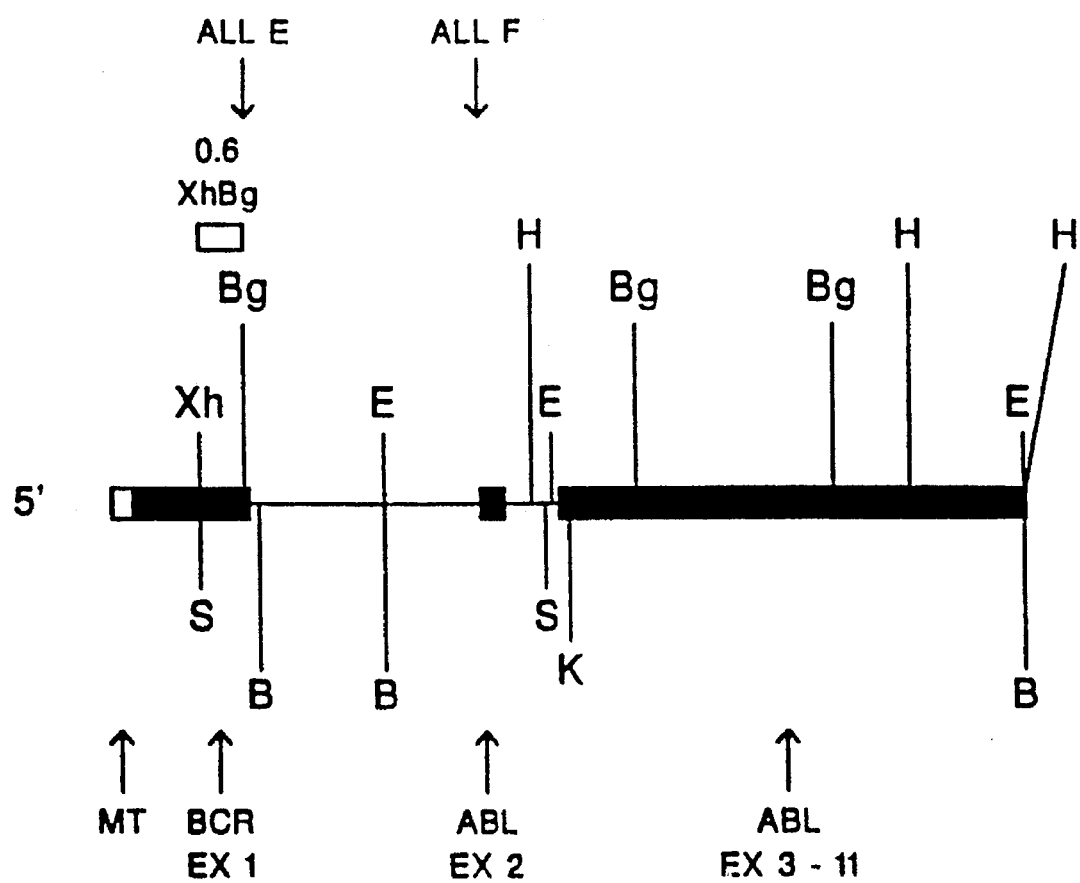
FIG. 2. P190-producing BCR/ABL construct as comprised in pALMP. Boxed areas indicate the position of coding sequences; the location of the MT promoter, BCR exon 1, ABL exon 2 and the main body of ABL exons is as indicated below the map. The location of the probe used in FIG. 3 (0.6 XhBg) is indicated above the map with a cross-hatched box. The arrows above the map point to the approximate locations of oligonucleotide primers, "ALL E" and "ALL F" (Kawasaki et al., 1989, Proc. Natl. Acad. Sci. U.S.A. 85:5698–5702). B=BamHI; Bg=BglII, E=EcoRI; H=HindIII; K=KpnI; S=SalI; Xh=XhoI.

After microinjection of this P190 construct into fertilized one-cell embryos, reimplantation and birth of pups, no transgenic progeny were obtained. To circumvent the possibility that its expression is lethal during embryogenesis a new construct was made, identical to the first except that the BCR promoter was replaced by the mouse metallothionine-1 (MT) promoter. This promoter was chosen, because it can be considered "housekeeping" in that it is expressed in nearly all tissues and, in addition, is inducible (Brinster et al., 1982, Nature 296:39–42). The final construct, termed PALMP (FIG. 2) consists of a segment of the MT promoter, from nucleotide −153 to +68 (Stuart et al., 1984, proc. Natl. Acad. Sci. U.S.A. 81:7318–7322), joined to the first exon of the BCR gene. The construct further contains segments of BCR intron 1, the pSK polylinker, a segment of ABL intron 1, exon 2, intron 2 and the remaining ABL coding sequences.

TRANSGENIC P190 MICE EXPRESS THE TRANSGENE

Figure 3:
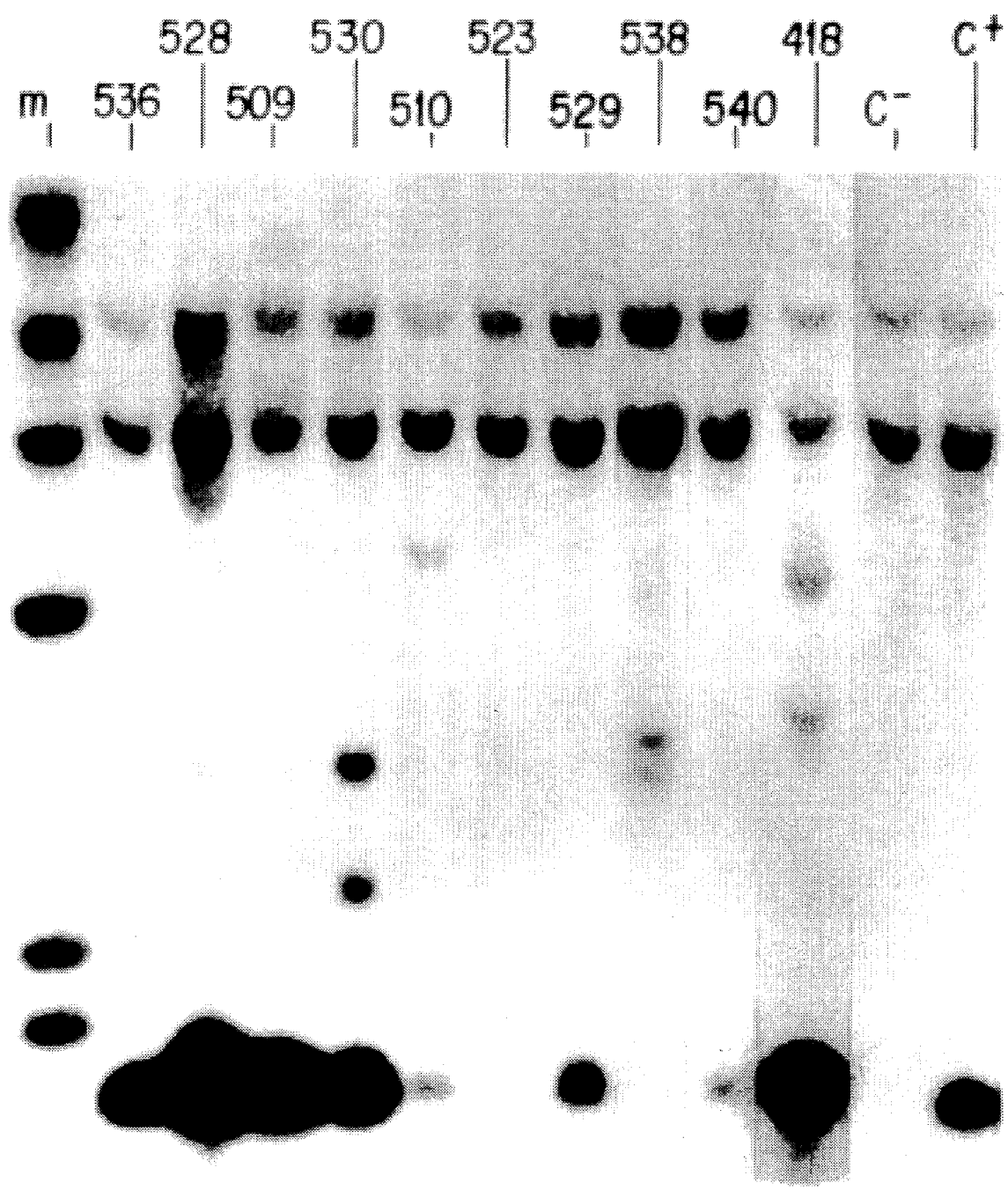
FIG. 3. Southern blot analysis of transgenic mice. Numbers above the lanes refer to the mice described in the text. DNAs were digested with BamHI. A λ/HindIII marker is shown to the left. C−=negative control; C+=positive control with 0.1 ng cloned DNA construct added in the digestion.

Using this construct, a total of 60 progeny mice were obtained; of these, 10 (16.6%) were found to be transgenic. Southern blot analysis on tail DNAs next to cloned DNA reference standards of known quantities (not shown) indicated that transgene copy numbers varied from an estimated 1 to 10 copies (see table 1). Multiple-copy transgenes appeared to consist of tandem, head-to-tail arrays of the construct (FIG. 3).

RNAs isolated from two animals (#418 and #509) which had exhibited distinct pathological symptoms (see below) were used to evaluate expression of the transgene. Since RNA was isolated post-mortem from the leg (including marrow, bone, blood and muscle) of animal #418, which had died, it was unsuitable for Northern blot analysis. Therefore, expression was examined using previously described (Kawasaki et al., 1988, Proc. Natl. Acad. Sci. U.S.A. 85:5698–5702) oligonucleotide primers (see FIG. 2), reverse transcriptase and the polymerase chain reaction. Although this method is not quantitative, it will allow the evaluation of the presence or absence of a transcript. The oligonucleotides should amplify a cDNA fragment of 307 bp in cells containing the 7.0 kb BCR/ABL chimeric mRNA.

Figure 4:
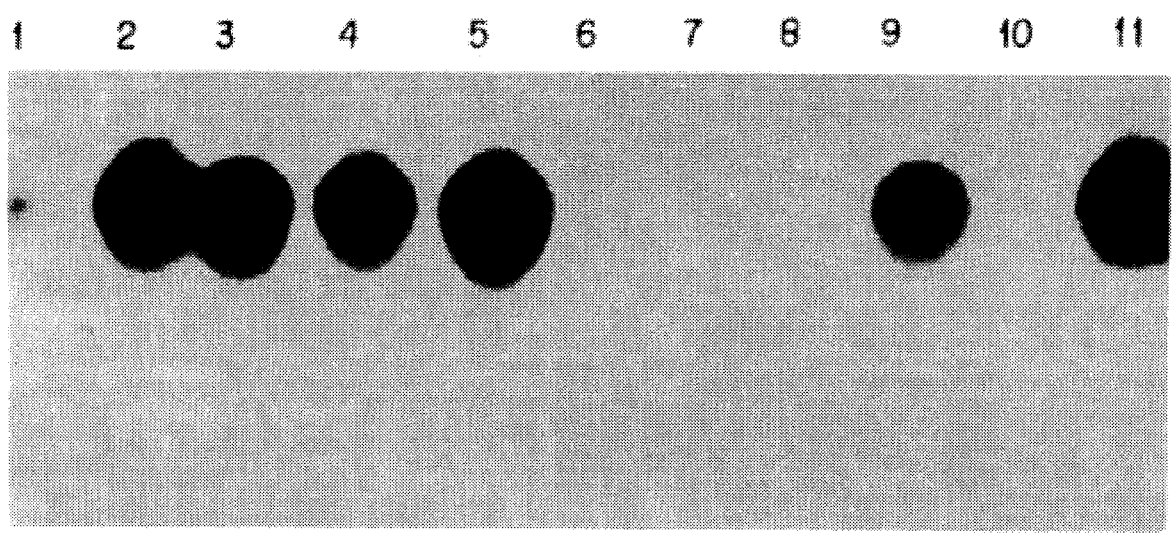
FIG. 4. Expression of the P190 BCR/ABL construct. RNAs used include those from heart, muscle, brain and spleen of mouse #509 (lanes 1–4); NIH 3T3 cells (lanes 6 and 8); control non-transgenic #417 RNA (lanes 7 and 10), NIH 3T3 cells transfected with P190/BCR (lane 9) and RNA from transgenic #418 (lane 11).

In RNA isolated from NIH 3T3 cells transfected with the P190/MT construct and the original P190/BCR construct this method detected the 307 bp fragment (FIG. 4, lanes 5 and 9). No signal is evident in untransfected NIH 3T3 control RNA (lanes 6 and 8). This indicates that the construct produces mRNA in the absence of intentional induction of the promoter with heavy metals. In the RNA of mouse #418, the 307 bp fragment is also clearly present (FIG. 4, lane 11). Control RNA isolated post-morten from a non-transgenic sibling (#417, lane 7 and 10) showed no signal. RNA was extracted from spleen, brain, heart, and muscle of mouse #509: expression was found in all these tissues (FIG. 4, lanes 1–4).

BCR/ABL TRANSGENIC MICE RAPIDLY DEVELOP ACUTE LEUKEMIA

To date of the ten transgenic animals, eight have died and two remain alive. Three animals (#418, 536 and 530) ranging in age from 10–13 days were found dead before peripheral white blood cell counts could be performed (Table 1). Four animals (#509, 510, 538, Five animals, (#509, 510, 538, 528, 529) were sacrificed when moribund. A pregnant female (mouse #528), died at 58 days while giving birth. It had a terminal blood cell count of $2.9 \times 10^9$/L. A small but significant percentage (approximately 5%) of peripheral blood white cells were lymphoblasts. All eight animals which died were autopsied and examined histopathologically. Interestingly, six animals (#530, 509, 510, 538, 529 and 528) were diagnosed as having ALL, while the remaining two (#418 and 536, both of which were found dead) were diagnosed after autopsy as having CML, in blast crisis.

PATHOLOGY OF LEUKEMIC MICE

Figure 5A:
FIG. 5A–5D. Pathology of CML, blast crisis mice. A. Gross anatomical picture of mouse #418. Note the presence of prominent tumor masses associated with the lymph nodes and soft tissues of the neck. B. Central nervous system of mouse #536. Note the extensive tumor involvement in the subarachnoid space of the brain (x120, hematoxylin and eosin [H and E]). C. Medium power view of soft tissue-associated tumor in mouse #418. Note the total involvement of soft tissue with neoplastic myeloid cells which are predominantly composed of myeloblasts and promyelocytes with varying lesser numbers of myelocytes and metamyelocytes (x640, H and E). D. Medium power view of leukemia-involved peripheral blood with leukemic myeloid cells which are predominantly composed of segmented polymorphonuclear neutrophils (PMNs) and lesser numbers of more undifferentiated forms (x640, H and E).
Figure 5B:
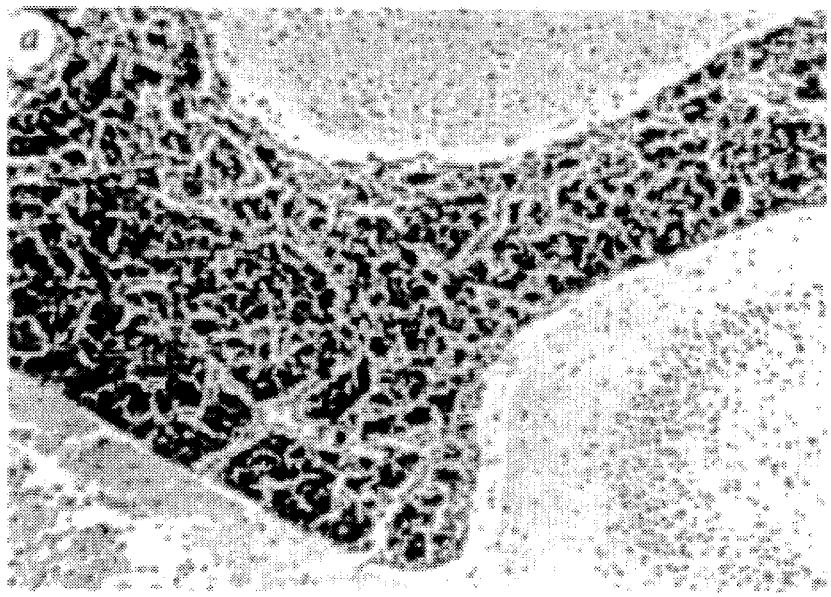
Figure 5C:
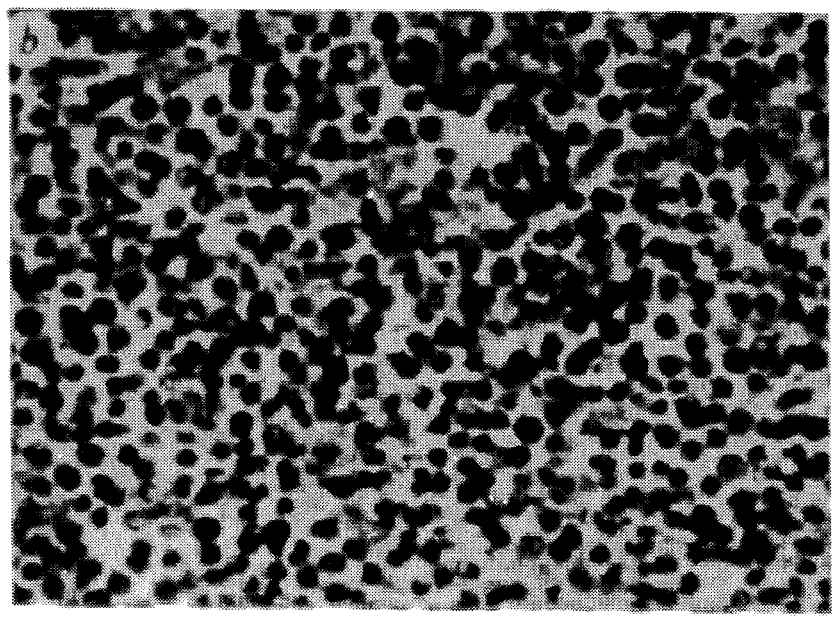
Figure 5D:
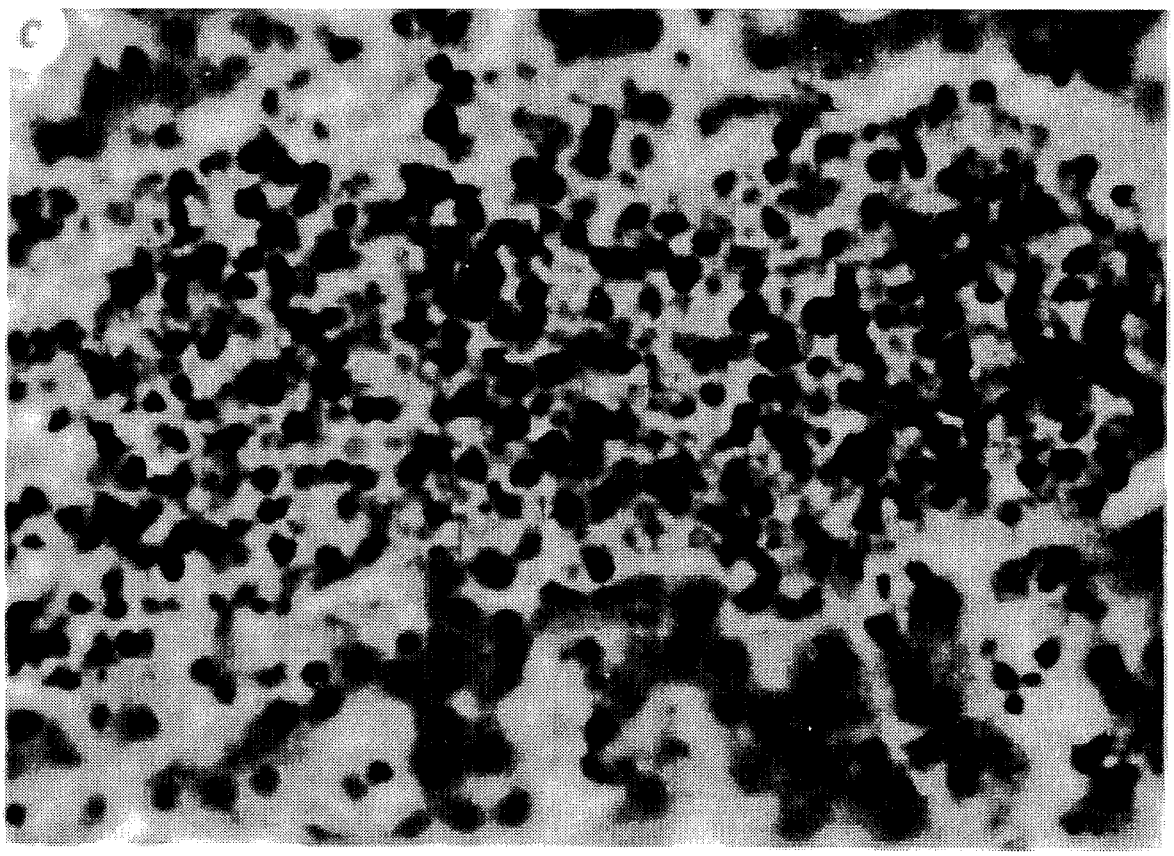

The hematopathologic features of these two leukemic processes are further detailed and summarized in Table 2. More specifically, mouse #418 demonstrated the presence of greatly enlarged neck masses (see FIG. 5A), which proved histopathologically to be either lymph nodes and/or subcutaneous tissue involved with neoplastic myelogenous leukemia cells (see FIG. 5C). The neck mass-associated leukemia cells were composed predominantly of primitive myeloid-type blasts (myeloblasts) with varying smaller numbers of promyleocytes, myelocytes and metamyelocytes (see FIG. 5C). These morphologic findings were also observed in bone marrow. In contrast to bone marrow and neck masses, peripheral blood from mouse #418, although markedly leukemic (see hepatic vein, FIG. 5D), demonstrated a predominance of segmented polymorphonuclear neutrophils (PMNs) with lesser numbers of more undifferentiated myeloid forms. Mouse #536, although not demonstrating enlarged neck masses, had similar morphologic findings (predominantly myeloid-type blasts with lesser numbers of more differentiated granulocytic forms) in its bone marrow. In addition, #536 demonstrated marked leukemic infiltration of the central nervous system (FIG. 5B). Taken together, mouse #418 and 536 were diagnosed as having CML, blast crisis (myeloid type).

TABLE I

COMBINED MOLECULAR, HEMATOLOGIC, AND PATHOLOGIC FINDINGS IN BCR/ABL TRANSGENIC MICE[1]

| ANIMAL # | TRANS-GENE COPY # | AGE AT DEATH (DAYS)[2] | WBC AT DEATH $(\times 10^9/l)$[3] | DIAGNOSIS |
|---|---|---|---|---|
| 1. 418 | 7 | 10 | ND | CML, blast crisis |
| 2. 536 | 4 | 13 | ND | CML, blast crisis |
| 3. 530 | 8 | 12 | ND | ALL |
| 4. 509 | 8 | 21 | 137 | ALL |
| 5. 510 | 2 | 28 | 40 | ALL |
| 6. 538 | 2 | 38 | 196 | ALL |
| 7. 529 | 3 | 43 | 347 | ALL |
| 8. 528 | 10 | 58 | 2.94 | ALL/LL |
| 9. 523 | 1 | alive | NA[4] | NA |
| 10. 540 | 1 | alive | NA[4] | NA |

[1]Abbreviations used: WBC = peripheral white blood cell count; ND = not done; NA = not applicable; CML = chronic myelogenous leukemia; ALL = acute lymphoblastic leukemia; LL = lymphoblastic lymphoma.
[2]Animals 418, 536 and 530 were found dead; animals 509, 510, 528, 529 and 538 were sacrificed when moribund.
[3]Preterminal WBC's: WBC of animal 510 $(\times 10^9/L) = 22.5$ on day 21 and 47.5 on day 25; WBC of animal 529 $(\times 10^9/L) = 13.2$ on day 28 and 297 on day 41; WBC of animal 538 $(\times 10^9/L) = 14.1$ on day 18, 20.1 on day 24 and 29.8 on day 37; WBC of animal 528 $(\times 10^9/L) = 18.1$ on day 28, 12.8 on day 41.
[4]Although mouse 523 and 540 are alive with normal WBC counts, a small but significant percentage (3–5%) of peripheral blood white cells were lymphoblasts.

Figure 6A:
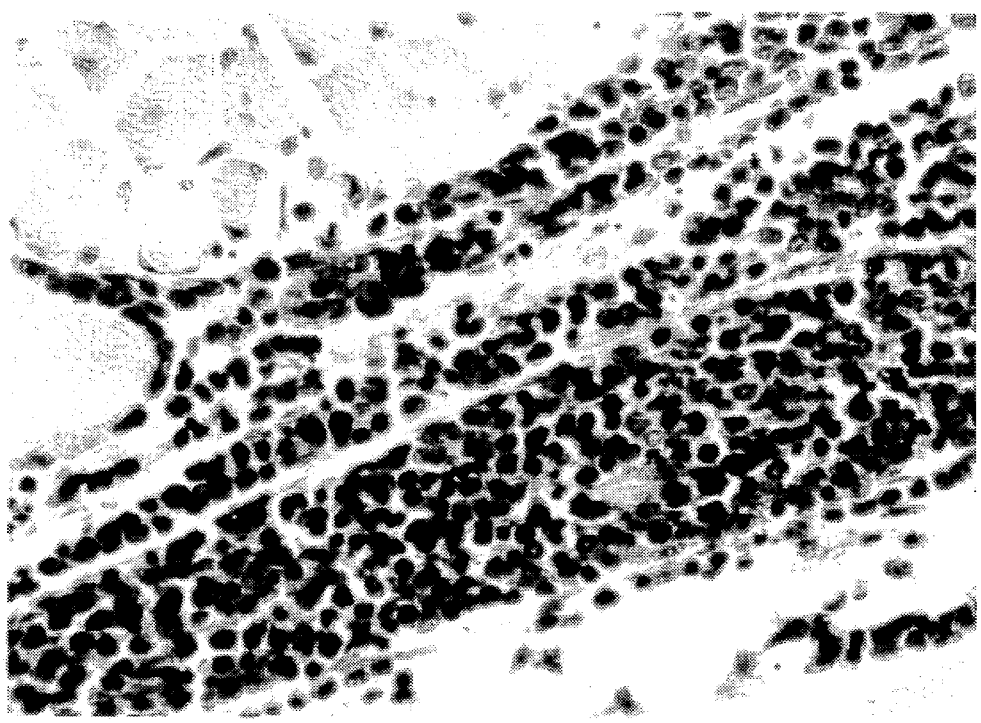
FIG. 6A–6D. Pathology of ALL mice. A Medium power view of involved bone marrow from mouse #509. Note the extensive involvement of marrow with primitive lymphoblasts with scant cytoplasm (x580, H and E). B. Medium power view of peritrabecular soft tissue. Note the extensive involvement of bone-associated soft tissue with primitive, neoplastic lymphoblasts which are invading between skeletal muscle fibers (x600, H and E). C. Medium power view of peripheral blood from mouse #538. Note the extensive involvement with primitive, neoplastic lymphoblasts which demonstrate primitive nuclear chromatin and scant cytoplasm (x620, Wright-Giemsa). D. higher power view of the same peripheral blood from mouse #538. Note the presence of a mitotic figure (x780, Wright-Giemsa).
Figure 6B:
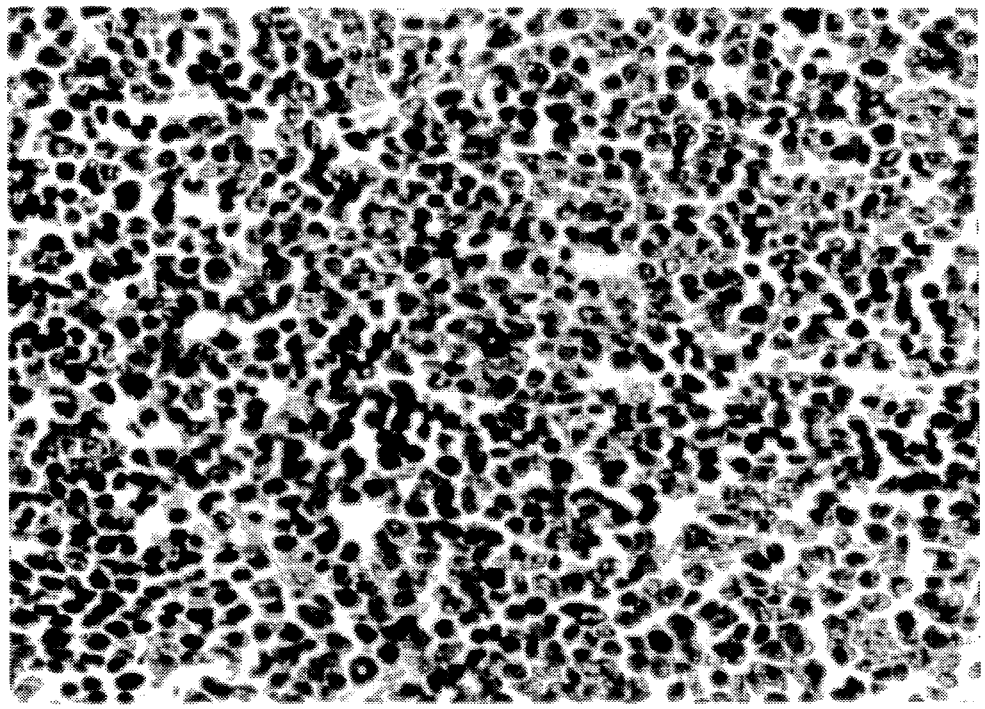
Figure 6C:
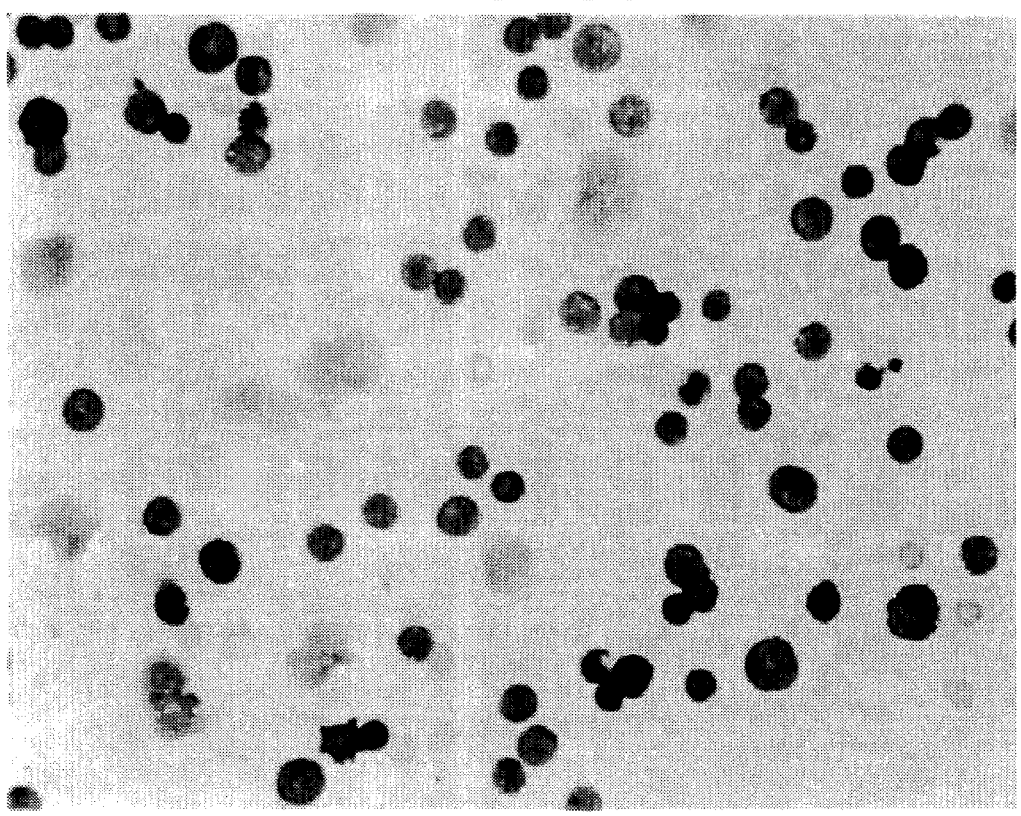
Figure 6D:
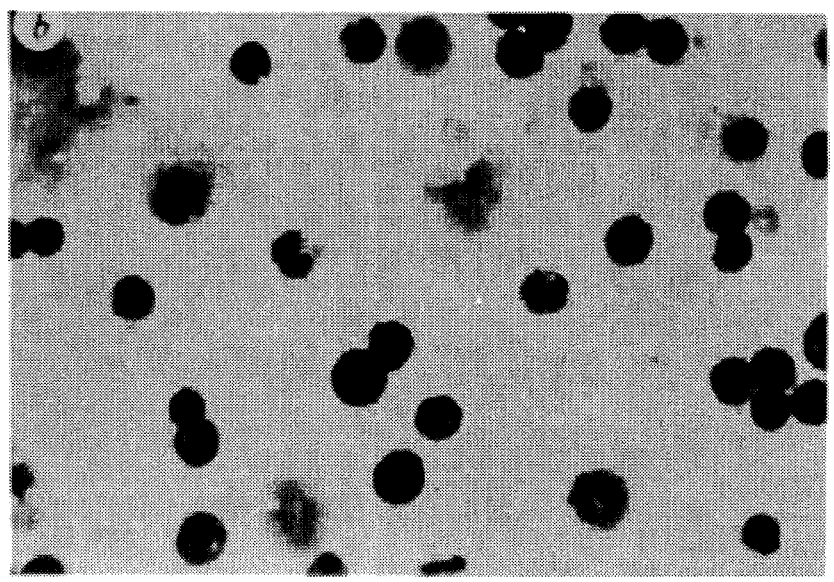
Figure 7A:
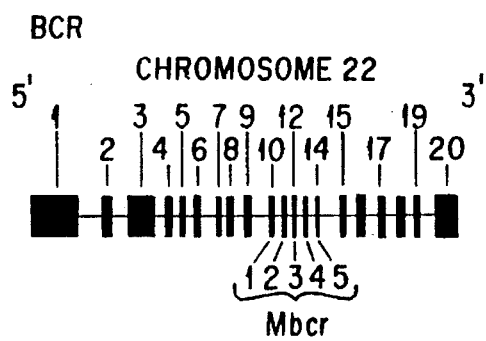
FIG. 7. Diagram of (a) BCR gene; (b) c-ABL gene; (c) a BCR/ABL gene fusuion on a Philadelphia chromosome from a patient with CML; and (d) a BCR/ABL gene fusion on a Philadelphia chromosome from a patient with ALL (see Kurzrock et al., 1988, N. Engl. J. Med. 319:990–997).
Figure 7B:
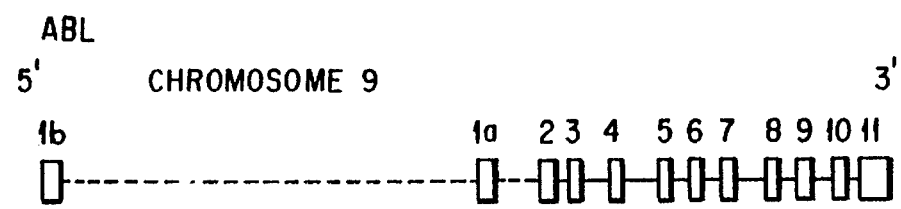
Figure 7C:
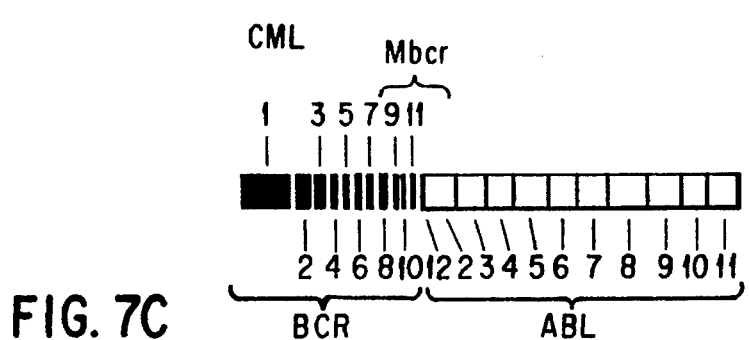
Figure 7D:
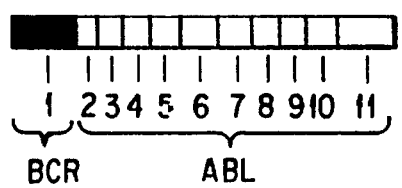
Figure 8:
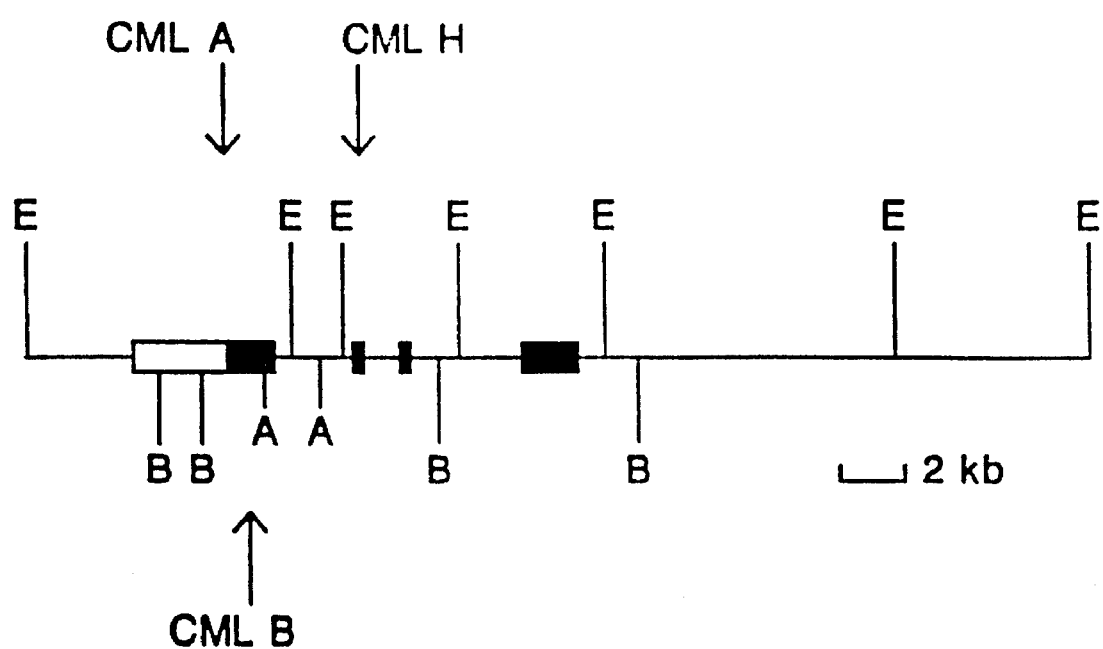
FIG. 8. The BCR/ABL c18(der) construct as comprised in pCLMP. The open box represents the BCR gene coding sequences; the solid boxes represent ABL coding sequences. A=Aa+II; B=BamHI; E=EcoRI.

In contrast, mouse #509, 530, 510, 538, 529 and 528 were observed to have bone marrows which were predominantly replaced with primitive lymphoblasts (see FIG. 6A). In addition, all six of these mice demonstrated peritrabecular invasion of neoplastic lymphoblasts into the surrounding skeletal muscle-containing soft tissues (FIG. 6B). All mice morphologically demonstrated peripheral blood involvement, with four mice (#509, 510, 538, 529) exhibiting markedly elevated peripheral blood WBC counts, which were predominantly composed of neoplastic, primitive lymphoblasts (FIG. 6C and 6D). Both the splenic white and red pulp were extensively involved with neoplastic lymphoblasts in mice #509, 510, 538 and 529. Taken together, five mice (#530, 509, 510, 538, 529) were easily diagnosed as having ALL. Mouse #528, although having morphologically detectable leukemia cell involvement of peripheral blood and spleen, had extensive bone marrow and lymph node involvement as well as histopathologically detectable subarachoid involvement of the central nervous system with neoplastic lymphoblasts. This mouse was therefore diagnosed as having acute lymphoblastic leukemia/lymphoblastic lymphoma (LL). In addition, the involvement of the thymus was not found in any of these six animals.

TABLE II

HEMATOPATHOLOGY OF ACUTE LEUKEMIA OCCURRING IN BCR/ABL TRANSGENIC MICE[1]

| Leukemia Type | Number of Animals | Morphology | Additional Comments |
|---|---|---|---|
| 1. CML, blast crisis (see FIG. 5) | 2 | Bone marrow, subcutaneous, and soft tissue contains a predominance of myeloid-type blasts with varying numbers of promyelocytes, myelocytes and metamyelocytes (see FIG. 5c); peripheral blood and spleen demonstrate marked leukemia with a predominance of segmented PMNs and lesser numbers of more un-differentiated forms (see FIG. 5D). | Involved subcutaneous soft tissues, lymph nodes, and central nervous system (see FIGS. 5A, B and C). |
| 2. ALL (see FIG. 6) | 6 | Bone marrow is virtually replaced with primitive lymphoblasts (see FIG. 6A), which also invade adjacent skeletal muscle in soft tissue (see FIG. 6B); spleen and peripheral blood demonstrate marked leukemia with a predominance of lymphoblasts (see FIG. 6C, D); mouse 528, although having minimal involvement of peripheral blood, had extensive marrow involvement as well as extensive lymph node involvement (i.e., leukemia/lymphoma. | In 2 animals tested, leukemic lymphoblasts stained positive on frozen spleen sections for the B220 antigen; of 4 animals tested (spleens), germline (unrearranged) configurations for Ig heavy chain genes were present in 3 animals; one animal showed a minor clone(s) of leukemic cells which had rearranged its Ig heavy chain genes; all 4 animals were germline for both kappa light chain and T cell receptor beta genes. |

[1]Abbreviations used: CML = chronic myelogenous leukemia; PMNs = polymorphonuclear neutrophils; ALL = acute lymphoblastic leukemia; Ig = immunoglobulin.

ACUTE LYMPHOBLASTIC LEUKEMIA IS PREDOMINANTLY NON-CLONAL

Preliminary genotype analysis was performed on leukemia-involved splenic tissue obtained from four ALL animals (#509, 510, 538 and 529 [see above]). Phenotypic analysis on available frozen tissue spleen sections from animals #509 and 510 demonstrated positive immunostaining for the B220 antigen on neoplastic lymphoblasts. Since B220 antigen is normally found on mouse pre-B cells as well as on more mature B cells (Coffman, 1983, Immunol. Rev. 69:5–23) it was of importance to determine if the B220+lymphoblasts had undergone clonal rearrangement(s) of their immunoglobulin genes. Southern blot analysis of genomic DNA from the spleens of these two (#509 and 510) as well as from a third (#538) animal demonstrated germline configurations for both the IgH (heavy chain) and kappa (light chain) genes (data not shown). In contrast, genomic DNA from the spleen of animal #529 showed the presence of a minor clone of pre-B cells (two faintly rearranged bands with the IgH (J-H) probe and unrearranged [germline]bands with the kappa light chain probe). The T-cell receptor β chain locus had a germline configuration in all four animals. In summary, preliminary phenotypic and/or genotypic evaluation of the ALL Mice is most likely consistent with the presence of a polyclonal population of neoplastic pre-B lymphoblasts.

DISCUSSION

In the experiments described herein, we have generated ten transgenic BCR/ABL P190 mice, eight of which died or were moribund with acute leukemia between 10 and 58 days after birth. Remarkably, two animals were diagnosed as having blast crisis CML while the remaining six had acute lymphoblastic leukemia (ALL). In addition to being extremely rapid in onset, both morphologic types of leukemia closely resembled the corresponding human disease.

In initial experiments, we have attempted to generate transgenic mice using BCR/ABL P210 or P190 constructs under control of the BCR gene promoter; however, live transgenic progeny were never obtained with either construct. In the construct used here, the expression of P190 was under control of a fragment of the MT promoter, which apparently was expressed late or not at all during embryogenesis. The MT promoter as a whole has been frequently used by others to generate transgenic mice; varying levels of spontaneous or inducible expression have been found in different tissues (for example, see Iwakura et al., 1988, EMBO J. 7:3757–3762). Upon transfection of NIH 3T3 cells, our construct had a basal level of spontaneous expression. In view of these data, it is probable that a low level of spontaneous transcription must have occurred in the transgenic mice. In addition, there appears to be some correlation between transgene copy number and severity or course of the disease, as the only two animals alive to date have a single copy of the transgene (see Table I). It is interesting that both mice with single transgenic copies, although alive with normal WBC counts, have a small but significant percentage of circulating lymphoblasts on peripheral blood smears. It appears that the transgene was expressed in the two animals tested representing both types of acute leukemia (CML blast crisis and ALL), although we cannot quantitatively compare the levels in these animals using the PCR/RT method on RNAs of different quality. Transcription was found in the heart, brain, muscle, spleen and liver of mouse #509. Although it is possible that these tissues actually transcribe the transgene, it is more likely that the observed expression originated from infiltrating or blood-vessel leukemia cells. The weak signal seen in the heart RNA prepraration may therefore be due to the fact that the animal was sacrificed by cardiac puncture and removal of blood from this organ.

The BCR gene, which contributes its promoter to the chimeric BCR/ABL gene in human Ph-positive leukemia is not expressed exclusively or in extremely high levels in bone marrow (Collins et al., 1987, Mol. Cell Biol. 7:2810–2876). The results presented here indicate, indeed, that its promoter is not necessary at all for leukemogenesis. Instead, it appears that the crucial contribution of the BCR gene consists of its 5' coding sequences and that its fusion of these sequences to human ABL produces a unique, leukemogenic protein. The properties of this protein must be closely related to its primary structure; recently, mice have been generated which were transgenic for a BCR/v-ABL P120 (lacking the murine exon 2 and part of exon 3) fused to most of the 5' BCR exons as found in CML. Of the 15 founder animals, three were moribund after 14, 55 and 77 days; the remaining animals were alive at 12 months of age and showed no signs of tumors; the type of malignancy generated by this transgene differs from that found in the present study in that only monoclonal B and T cell lymphomas were found (Hariharan et al., 1989, Mol. Cell Biol. 9:2798–2805).

Although it superficially appears that two completely different morphologic types of acute leukemia (lymphoid and myeloid) were generated in BCR/ABL transgenic mice, previous work in both man and mouse supports a close relationship between B-lymphoid and myeloid cells. It is well known that human chronic myelogenous leukemia often evolves to a pre-B lymphoblast crisis (Bakhsi et al., 1983, N. Engl. J. Med. 309:826–831; Vogler et al., 1979, Blood 54:1164–1170). Hematopoeitic cells transformed in vitro by RAS oncogene-containing retroviruses coexpress pre-B and myeloid cell phenotypes suggesting that a progenitor cell for both B lymphocytes and myeloid cells (primarily granulocyte [G]/monocytes [M]) exists (Holmes et al., 1986, J. Exp. Med. 164:443–457). Further evidence for the existence of a common progenitor cell, termed pro G/M/B, is provided by a variety of in vitro studies which demonstrate differentiation of lymphoid-like progenitor cells into macrophages (Davidson et al., 1988, J. Exp. Med. 168: 389–407; Bauer et al., J. Immunol. 136:4695–4699; Hanecak et al., 1989, Mol. Cell Biol. 9:2264–2268). It is therefore not surprising that both types of leukemia were observed in BCR/ABL transgenic mice.

Since three of the affected mice died between 10–13 days of age, it is possible that they may have been preleukemic in utero. Four other mice were overtly leukemic at 21, 28, 38 and 43 days. The remaining mouse had overt leukemia/lymphoma at 58 days. If one considers, that one mouse year is roughly equivalent to 33 human years, the ranges in the ages at death would correspond from 11 months to 5 years in human age. In the human, the majority of children with Ph-positive ALL are pre-B in immunotype (Ribeiro et al, 1987, Blood 7.0:948–951) and predominantly appear to have the type of translocation which produces P190 (Heisterkamp et al., 1989, Blood 73:1307–1311). The P190 fusion protein may therefore be involved in a very agressive type of leukemia with an early onset and rapid progression. Indeed, the association of the P190 protein with a more aggressive type of disease is supported by experiments, in which the effects of P190 and P210 on immature lymphoid cells were compared: P190 appears to stimulate the growth of immature lymphoid cells more strongly than the P210 in mouse bone marrow cultures (Mol. Cell Biol. 9:1866–1874).

From the results presented in this study one major conclusion can be drawn: the BCR/ABL hybrid oncogene is causally associated with rapid-onset acute leukemia in transgenic mice which closely mimic the human diseases CML and ALL. Moreover, the rapid induction time, as well as the finding of polyclonality within the presumed pre-B cell population argues that a secondary event was probably not necessary to generate overt leukemia. In this respect, the P190 found in association with Ph-positive ALL could differ from our mouse model: in Ph-positive, P190 producing ALL, the Ph-chromosome is often neither the sole nor the first chromosomal abnormality present in the leukemic cells of the patients (Dameshek and Gunz, 1983, in "The Nature of Leukemia" Gunz and Henderson Eds., Grune and Stratton publ. p. 182). Our results indicate however, that the Ph-chromosome alone may be sufficient to cause acute leukemia.

The availability of a mouse model for Ph-positive leukemia should enable us to study many aspects of this disease, from preleukemia to progression, which would otherwise be difficult to follow. In addition, the availability of a mouse model should also allow a rapid evaluation of therapeutic protocols and chemotherapeutic agents for this type of leukemia.

DEPOSIT OF MICROORGANISMS

The following recombinant plasmid was deposited with the Agricultural Research Culture Collection (NRRL) in Peoria, Ill.:

|  |  | NRRL Accession No. |
|---|---|---|
| plasmid | pALMP | B-18563 |
| plasmid | pCLMP | B-18564 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A transgenic mouse which carries a BCR/C-ABL transgene that comprises at least the first exon of a BCR gene and a functional portion of a c-ABL gene under the control of a metallothionine promoter sequence in its somatic and germ cells, whereby said BCR/c-ABL transgene is expressed in its bone marrow cells and is effective for promoting a leukemia in said mouse.

2. The transgenic mouse of claim 1 in which the BCR/c-ABL transgene comprises non-human c-ABL sequence.

3. The transgenic mouse of claim 1 in which the BCR/c-ABL transgene comprises human c-ABL sequence.

4. The transgenic mouse of claim 1 in which the BRC/c-ABL transgene further comprises a portion of the third exon of the c-ABL gene.

5. The transgenic mouse of claim 1 in which the BCR/c-ABL transgene further comprises the second exon of the c-ABL gene.

6. The transgenic mouse of claim 2 in which the BCR/c-ABL transgene further comprises an exon of the Mbcr region of the BCR gene.

7. The transgenic mouse of claim 3 in which the BCR/c-ABL transgene further comprises an exon of the Mbcr region of the BCR gene.

8. The transgenic mouse of claim 1, 2, or 3 in which the BCR/c-ABL transgene further comprises exons two through eleven of the c-ABL gene.

9. The transgenic mouse of claim 1, 2, in or 3, in which the BCR/c-ABL transgene further comprises an exon of the Mbcr region of the BCR gene and exons two through eleven of the c-ABL gene.

10. The Mouse of claim 6 or 7 in which the BCR/c-ABL transgene is effective for promoting a chronic myelocytic leukemia in said mouse.

11. The mouse of claim 1 in which the BCR/c-ABL transgene is effective for promoting an acute lymphoblastic leukemia in said mouse 12. The mouse of claim 1, wherein said mouse is produced using embryonic stem cells into which the BCR/c-ABL transgene has been introduced.

13. The transgenic mouse of claim 10 wherein said BCR/c-ABL transgene comprises human c-ABL sequence.

14. The transgenic mouse of claim 11 wherein said BCR/c-ABL transgene comprises human c-ABL sequence.

15. The transgenic mouse of claim 12 wherein said BCR/c-ABL transgene comprises human c-ABL sequence.

* * * * *